United States Patent [19]

Lassen et al.

[11] Patent Number: 4,650,900
[45] Date of Patent: Mar. 17, 1987

[54] AMINOALKYL SUBSTITUTED UREA DERIVATIVES AND METHOD OF TREATMENT

[75] Inventors: Niels Lassen, Gentofte; Klaus P. Bogeso, Lyngby; Klaus G. Jensen, Frederiksberg, all of Denmark

[73] Assignee: H. Lundbeck A/S, Copenhagen-Valby, Denmark

[21] Appl. No.: 814,664

[22] Filed: Dec. 30, 1985

[30] Foreign Application Priority Data

Jan. 10, 1985 [GB] United Kingdom ............... 8500615

[51] Int. Cl.$^4$ .................. C07C 127/17; C07D 239/02
[52] U.S. Cl. ..................... 564/56; 546/332; 548/567; 514/331; 514/408; 514/428; 514/595
[58] Field of Search ............... 564/56; 514/595, 331, 514/408, 428; 546/332; 548/561, 567

[56] References Cited

U.S. PATENT DOCUMENTS 3,388,158  6/1968  Surrey .................................. 564/56
4,216,228  8/1980  Yamada et al. ...................... 564/56

*Primary Examiner*—Charles F. Warren
*Assistant Examiner*—Elizabeth A. Flaherty
*Attorney, Agent, or Firm*—Gordon W. Hueschen

[57] ABSTRACT

The present invention relates to novel amino alkyl substituted urea derivatives as well as their acid addition salts with pharmaceutically acceptable acids, to methods for the preparation of said derivatives and pharmaceutical compositions containing same, and a method for the treatment of tumors therewith.

The novel urea derivatives have shown pronounced anti-neoplastic activity when tested against various tumor models in animals.

The novel compounds of the present invention may be represented by the following formula:

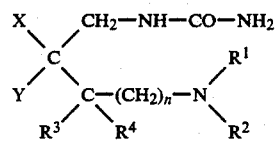

wherein X and Y are the same or different and are selected from the group consisting of a phenyl group, each of said phenyl groups being optionally substituted with one or two groups selected from halogen, $CF_3$, OH, or alkoxy (1–4 C-atoms); and $R^1$ and $R^2$ are the same or different, and are each selected from the group consisting of lower alkyl groups having from one to four carbon atoms inclusive, or they form together with the nitrogen atom a saturated five- or six-membered heterocyclic ring; $R^3$ and $R^4$ are each selected from hydrogen, lower alkyl or alkenyl groups with from 1–6 carbon atoms inclusive, cyclopentyl or cyclohexyl; and n is 0 or 1, as well as pharmaceutically acceptable acid addition salts thereof.

When X is different from Y and/or $R^3$ is different from $R^4$ the compounds of Formula I exist as optical isomers, which may be separated in the individual enantiomers, which often show the activity in different degree. These individual isomers as well as their isolation fall within the scope of the present invention.

9 Claims, No Drawings

AMINOALKYL SUBSTITUTED UREA DERIVATIVES AND METHOD OF TREATMENT

BACKGROUND OF THE INVENTION

Some urea derivatives having nitroso and chloroethyl groups attached to the one or both of the nitrogen atoms of the urea-molecule have been suggested and also sometimes found useful in the treatment of various tumours, either alone or in combination with other cytostatic drugs. Recently such derivatives known from U.S. Pat. No. 4,301,287 have been suggested. Such nitroso- and chloroethyl-derivatives have, however, various serious side effects, and some are rather toxic compounds, and the therapeutic index, the ratio between the toxic dose and the therapeutic dose, is not very favorable.

SUMMARY OF THE INVENTION

According to the present invention it has now surprisingly been found that the compounds of Formula I, as well as their acid addition salts, in animal experiments show promising cytostatic effects and have comparatively low acute toxicity. They act in all probability by a new mechanism which makes them promising as cytostatic drugs. Some of them have shown cytostatic effects in preliminary clinical trials.

Based upon the animal experiments the preferred compounds of this invention are those of Formula I in which X and Y are unsubstituted phenyl groups or phenyl groups having chlorine or fluorine atoms at the para-position; $R^1$ and $R^2$ are methyl groups; $R^3$ is a methyl or ethyl group, $R^4$ is hydrogen and n is 0 or 1.

When $R^1$ and $R^2$ together with the nitrogen atoms form a saturated five- or six-membered heterocyclic ring, such rings are preferably selected from pyrrolidine, piperidine, morfoline, thiomorfoline or N-lower alkyl-piperazine rings, said heterocyclic rings being optionally substituted with lower alkyl groups having from one to four carbon atoms inclusive.

The present invention also includes pharmaceutically acceptable acid addition salts of the compounds of Formula I. Such salts are easily prepared by methods known to the art. The base of Formula I is reacted with either the calculated amount of organic or inorganic acid in an aqueous miscible solvent, such as acetone or methanol, with isolation of the salt by concentration and cooling or an excess of the acid in aqueous inmiscible solvent, such as ethylether or chloroform, with the desired salt separating directly. Exemplary of such organic salts are those with maleic, fumaric, benzoic, ascorbic, embonic (pamoic), succinic, oxalic, bis-methylene-salicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glyconic, p-aminobenzoic and benzene sulfonic acids. Exemplary of inorganic salts of the compounds of Formula I are those with hydrochloric, hydrobromic, sulfuric, sulfamic, phosphoric and nitric acids. Of course, these salts may also be prepared by the classical method of double decomposition of appropriate salts which is wellknown to the art.

The compounds of Formula I and the non-toxic acid addition salts thereof may be administered both orally and parenterally, either alone or in combination with other cytostatic drugs, for example in the form of tablets, capsules, powders, syrups or solutions or suspensions for injection.

The present invention moreover comprises a method for the preparation of the urea derivatives of Formula I whereby a compound of the following formula

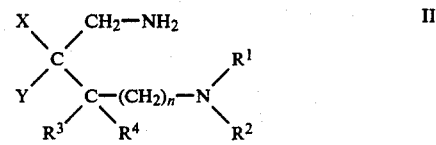

wherein X, Y, $R^1$, $R^2$, $R^3$, $R^4$ and "n" are defined above, is reacted with an alkali metal cyanate in an aqueous acid medium, whereupon the compound of Formula I formed by the reaction is isolated either as the free base or in the form of a pharmaceutically acceptable acid addition salt thereof, and in the case where the compound of Formula I exists as optical isomers, optionally the individual enantiomers are isolated in wellknown manner.

The reaction according to the method of the invention is preferably carried out in water possibly mixed with a lower alcohol at room temperature and at about neutral reaction. Preferably potassium cyanate is used but other sources of the cyanate ion may function equally well. The reaction conditions, however, may be varied in manners wellknown to the art for this type of reaction.

The starting materials of Formula II are partly known, for instance from U.S. Pat. No. 4,301,287 or from German Pat. Nos. 2,438,965 and 2,438,966. Some of the starting materials, however, are novel compounds but are prepared as described in the above-mentioned U.S. Patent.

The intermediates of Formula II may preferably be prepared according to the following reaction schemes:

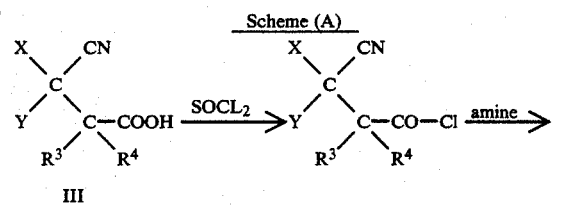

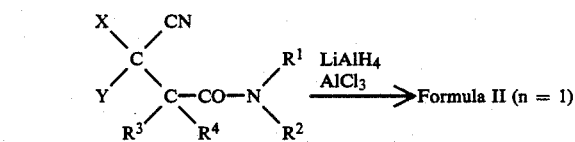

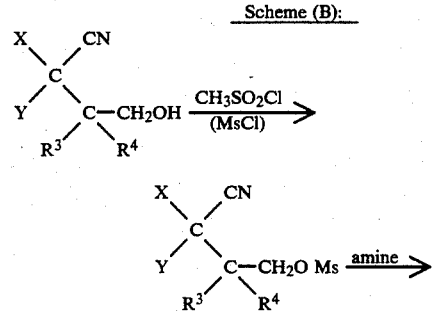

-continued
Scheme (B):

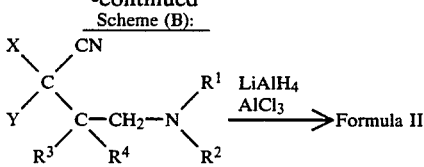

Scheme (C)

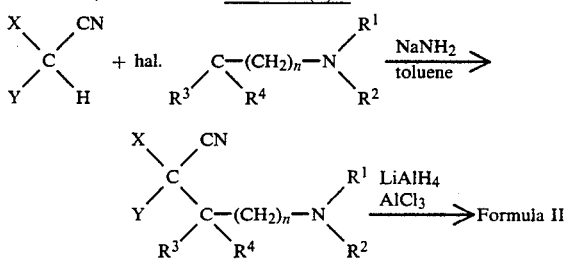

If one of $R^3$ and $R^4$ or both are other than hydrogen, method A or B will be preferred in order to avoid the contamination of the desired intermediate of Formula II with position isomers.

The following specific examples are given to illustrate the method of the present invention but, they are to be understood as exemplary only and are not to be construed as limiting.

STARTING MATERIALS

The starting materials of formula III (scheme A) are partly known and were prepared by a method described by F. Salmon-Legagneur et al. in the Bull.Soc. Chim. 1959, pg. 1958–63 and Compt.Rend. 250, pg. 4006–08, 1960, with a slight modification.

The compounds of formula III, where X and Y both are phenyl groups and $R^3$ and $R^4$ are both methyl groups or $R^3$ is a methyl, ethyl or n-propyl group and $R^4$ is hydrogen, are all known from said papers.

In a similar manner were prepared:
3-Cyano-3,3-diphenyl-2-hexyl-propionic acid. MP: 135°–136° C.
3-Cyano-3,3-diphenyl-2-cyclohexyl-propionic acid. MP: 226°–229° C.
3-Cyano-3,3-diphenyl-2-isopropyl-propionic acid. MP: 188°–191° C.

EXAMPLE 1

To a solution of 96.5 g (0.5 mol) of diphenylacetonitrile in 400 ml of dry dimethylformamide were added under nitrogen atmosphere and stirring and cooling 60 g (0.535 mol) of potassium tert. butoxyde keeping the temperature under 30° C. Thereupon were added dropwise 126 g (0.5 mol) of alphabromocaprylic acid ethyl ester at 20°–30° while cooling and stirring, whereupon the reaction mixture was stirred for further 2 hours at room temperature.

The mixture was poured into 2 liters of ice water, extracted with ether; the etherphase was separated, washed twice with 500 ml water, dried over $MgSO_4$, filtered and evaporated in vacuo.

To the residue were added 600 ml of ethanol and 42 g (0.75 mol) of potassium hydroxide, and the mixture was refluxed for 8 hours. The major part of the ethanol was evaporated in vacuo, the residue was poured into 1 liter of water, the mixture made acid with 75 ml of concentrated hydrochloric acid and extracted with ether. The etherphase was dried over magnesium sulphate, filtered and evaporated. The residue was dissolved in cyclohexane and cooled, whereupon 3-cyano-3,3-diphenyl-2-hexyl-propionic acid crystallized. Yield: 98 g (74%). MP: 135°–136° C.

The following reactions i.e. the preparation of acid chlorides and amides may be illustrated in the following way:

EXAMPLE 2

Preparation of acid chlorides

A mixture of 0.1 mol of the acid, 20 ml thionyl chloride and 50 ml of chloroform was heated under reflux for one hour, whereupon the mixture was evaporated thoroughly in vacuo at 60° C.

EXAMPLE 3

Preparation of 3-cyano-3,3-diphenyl-2-ethyl-N,N-dimethyl-propanamide

A solution of 3-cyano-3,3-diphenyl-2-ethylpropionyl chloride (0.1 mol prepared from 0.1 mol of the acid as described above) in 100 ml of methylen chloride was added dropwise while stirring to a mixture of 65 ml of 33% aqueous dimethylamine (ca. 0.5 mol) and 100 g of crushed ice. The mixture was stirred for 1 hour at room temperature, whereupon the organic phase was separated and washed with dilute hydrochloric acid. After drying over magnesium sulphate, filtration and evaporation, the residue was crystallized from a mixture of methylene chloride and ether. Yield: 28 g (88%) of the amide as a white crystalline substance melting at 170°–172° C.

The following propanamides were prepared in a similar manner:
3-Cyano-3,3-diphenyl-2-methyl-N-morpholino-propanamide. MP: 210°–215° C. (from diethylether)
3-Cyano-3,3-diphenyl-2-n-propyl-N,N-dimethyl-propanamide. MP: 160°–162° C.
3-Cyano-3,3-diphenyl-2-n-hexyl-N,N-dimethyl-propanamide, oil.
3-Cyano-3,3-diphenyl-2-cyclohexyl-N,N-dimethyl-propanamide. MP: 185°–187° C. (from ethanol).
3-Cyano-3,3-diphenyl-2-isopropyl-N,N-dimethyl-propanamide. MP: 136°–138° C. (from ethanol).
3-Cyano-3,3-diphenyl-2,2-dimethyl-N,N-dimethyl-propanamide, oil.

EXAMPLE 4

3-Cyano-3,3-diphenyl-2-methyl-N,N-diisopropyl-propanamide 0.1 Mol of 3-cyano-3,3-diphenyl-2-methylpropionyl chloride were added dropwise while cooling and stirring to 50 g (0.5 mol) of diisopropylamine. The mixture was left standing at room temperature overnight and heated at 40°–50° C. for 30 minutes. The mixture was poured into water and isolated as described above for the preparation of 3-cyano-3,3-diphenyl-2-ethyl-N,N-dimethyl-propanamide. The amide was crystallized from a mixture of toluen and ether. Yield: 25 g (50%), melting at 195°–205° C.

In a similar manner was prepared:
3-Cyano-3,3-diphenyl-2-methyl-N-tert.butyl-propanamide. MP: 210°–220° C.

EXAMPLE 5

2,2-Diphenyl-3-ethyl-4-dimethylamino-butanenitrile

3-Cyano-3,3-diphenyl-2-ethyl-propionyl chloride was prepared from the acid as described in Example 2 and reduced to 2,2-diphenyl-3-ethyl-4-hydroxy-butanenitrile as described in J.Med.Chem. 16, pg. 782–86 (1973) for 2,2-diphenyl-3-methyl-4-hydroxy-butanenitrile starting from 3-cyano-3,3-diphenyl-2-methylpropionic acid. The hydroxy compound was obtained after evaporation of a solution in diisopropylether as a yellow oil and used in the next step without further purification.

180 grams of 2,2-diphenyl-3-ethyl-4-hydroxy-butanenitrile were dissolved in 400 ml of dry pyridine. While stirring and cooling 100 gr of methansulfonyl-chloride were added drowpise at 0°–5° C., whereupon the mixture was stirred for 2 hours at room temperature. The mixture was poured into 3 liters of icewater and extracted with methylene chloride. The organic phase was washed with cold dilute hydrochloric acid, dried over magnesium sulfate, filtered and evaporated in vacuo. The residue was crystallized from diethyl ether. Yield: 135 g (58%); MP: 115°–117° C., of the methansulfonate of 2,2-diphenyl-3-ethyl-4-hydroxybutanenitrile.

A mixture of 20 g (0.06 mole) of this methanesulfonate and 50 ml of a 33% solution of dimethylamine (0.3 mole) in ethanol was heated for 16 hours in an autoclave at 110°–115° C. After cooling the mixture was poured into water and extracted with ether. The etherphase was extracted with dilute hydrochloric acid, whereupon the base formed was precipitated with dilute sodium hydroxide solution. The base was extracted with ether, the etherphase dried over potassium carbonate, filtered and evaporated. 18 g of 2,2-diphenyl-3-ethyl-4-dimethylaminobutanenitrile were obtained as a yellow oil which was used without further purification in the next step.

When using in this example, 25 g of pyrrolidine in stead of the ethanolic solution of dimethylamine, and heating the reaction mixture for 1 hour under reflux there was obtained 2,2-diphenyl-3-ethyl-4-(1-pyrrolidinyl)-butanenitrile as a white crystalline substance melting at 90° C. after crystallization from diethylether.

Of the further starting materials, 2,2-diphenyl-3-methyl-4-dimethylaminobutanenitrile and 2,2-Diphenyl-4-methyl-4-dimethylamino-butanenitrile were prepared according to the literature (J.Am.Chem.Soc., 69, 2454, 1947). The corresponding 2,2-Bis(4-fluorophenyl)-derivatives were prepared in the same manner from Bis(4-fluorophenyl)acetonitrile.

2,2-Bis(4-fluorophenyl)-3-methyl-4-dimethylamino-butanenitrile. Boiling point: 170° C./0.5 mmHg.

The 1,4-butanediamines and 1,5-pentanediamines of Formula II were prepared by reduction of the corresponding nitriles with $LiAlH_4/AlCl_3$ as described in the following example:

EXAMPLE 6

$N^4,N^4$-Dimethyl-2,2-diphenyl-3-methyl-1,4-butanediamine

A solution of 171 g of aluminiumchloride in 400 ml diethylether is added dropwise, while cooling and stirring, to 50 g of lithium aluminium hydride in 2 liters of diethylether. The solution is stirred at 20° C. for 15 minutes. A solution of 300 g of 2,2-diphenyl-3-methyl-4-dimethylaminobutanenitrile in 300 ml of diethylether is added dropwise under reflux. The reaction mixture is stirred with reflux for 3.5 hrs. The reaction mixture is then hydrolysed by dropwise addition of 1 liter 9N sodiumhydroxide. The organic phase is decanted, and the remaining salts are washed twice with 500 ml diethylether. The combined etherphase is dried with magnesium sulphate, filtered and evaporated in vacuo to give 280 g of an oil. The oil is taken up in 1 liter of acetone and 500 ml of ethanole, and oxalic acid is added till a pH of 3 is reached. After filtration and drying there are obtained 420 g of $N^4,N^4$-dimethyl-2,2-diphenyl-3-methyl-1,4-butanediamine as the dioxalate, melting at 187°–189° C.

In a similar way were prepared:

$N^4,N^4$-dimethyl-2,2-bis(4-fluorophenyl)-3-methyl-1,4-butanediamine, dioxalate, melting at 170°–175° C.

The following amine is a known substance (GER.-OFFEN. Nos. 24 38 965 and 24 38 966):

$N^4,N^4$-dimethyl-2,2-diphenyl-1,4-butanediamine.

EXAMPLE 7

$N^4,N^4$-diisopropyl-2,2-diphenyl-3-methyl-1,4-butanediamine

This compound was prepared from 3-cyano-3,3-diphenyl-2-methyl-N,N-diisopropyl-propanamide, essentially as described in Example 6, but per mole of starting material are used 3 moles of $LiAlH_4$ and 3 moles of $AlCl_3$, and the amide is added slowly to the reducing agent under reflux and while stirring, whereupon the mixture was refluxed for 8–16 hours.

In order to remove unused starting material, the base formed was extracted with dilute hydrochloric acid after hydrolysis with sodium hydroxide solution, and was precipitated again with sodium hydroxide solution. The diamine was gained as a yellow oil.

In a corresponding manner were obtained:

$N^4,N^4$-dimethyl-2,2-diphenyl-3-ethyl-1,4-butanediamine;

$N^4$-t.butyl-2,2-diphenyl-3-methyl-1,4-butanediamine;

2,2-Diphenyl-3-methyl-4-morpholino-butylamine;

$N^4,N^4$-dimethyl-2,2-diphenyl-3-propyl-1,4-butanediamine;

$N^4,N^4$-dimethyl-2,2-diphenyl-3-hexyl-1,4-butanediamine;

$N^4,N^4$-dimethyl-2,2-diphenyl-3-cyclohexyl-1,4-butanediamine;

$N^4,N^4$-dimethyl-2,2-diphenyl-3-isopropyl-1,4-butanediamine;

$N^4,N^4$-dimethyl-3,3-dimethyl-2,2diphenyl-1,4-butanediamine.

EXAMPLE 8

N-(4-Dimethylamino-2,2-diphenyl-3-methyl-1-butyl)-urea (Lu 9-110)

A solution of 120 g of potassium cyanate in 200 ml of water was added while stirring to a solution of 220 g of $N^4,N^4$-dimethyl-2,2-diphenyl-3-methyl-1,4-butanediamine in 1000 ml of water and 200 ml of concentrated hydrochloric acid at room temperature. The reaction mixture was stirred at room temperature for 30 minutes, filtered, and made basic with 9N sodiumhydroxide. The crystalline product was filtered and washed with water. The product was taken up in 1 liter of methanol and 200 ml water, and then 70 ml of glacial acetic acid were added. The solution was filtered, and 25% ammonium hydroxyde was added dropwise to pH=9. The product was filtered and washed successively with 500 ml methanol, 500 ml water and 500 ml methanol. The product was dried overnight in vacuo at 70° C. Yield: 204 g of pure N-(4-dimethylamino-2,2-diphenyl-3methyl-1-butyl)urea as a white powder, melting at 226°–228° C.

The following compounds were made in a similar way:

N-(4-Dimethylamino-2,2-diphenyl-1-butyl)-urea (Lu 17-009). MP: 190°–193° C.

N-(4-Dimethylamino-2,2-bis(4-fluorophenyl)-3-methyl-1-butyl)-urea (Lu 16-005). MP: 208°–210° C.

N-(4-(1-morfolinyl)-2,2-diphenyl-3-methyl-1-butyl)-urea. (Lu 22-030). MP: 115°–130° C.

N-(4-diisopropylamino-2,2-diphenyl-3-methyl-1-butyl)urea. (Lu 22-026). MP: 185°–187° C.

N-(4-dimethylamino-2,2-diphenyl-3-ethyl-1-butyl)urea. (Lu 22-027). MP: 143°–145° C.

N-(4-tert.-butylamino-2,2-diphenyl-3-methyl-1-butyl)urea. (Lu 22-042). MP: 163°–165° C.

N-(4-dimethylamino-2,2-diphenyl-3-propyl-1-butyl)urea. (Lu 22-063). MP: 151°–154° C.

N-(4-dimethylamino-2,2-diphenyl-3-hexyl-1-butyl)urea. (Lu 22-065). MP: 143°–146° C.

N-(4-dimethylamino-2,2-diphenyl-3-cyclohexyl-1-butyl)urea. (Lu 22-089). MP: 184°–192° C.

N-(4-dimethylamino-2,2-diphenyl-3-isopropyl-1-butyl)urea. (Lu 22-090). MP: 150°–159° C.

N-(4-(1-pyrrolidinyl)-2,2-diphenyl-3-ethyl-1-butyl)urea. (Lu 22-099). MP: 120°–130° C.

N-(4-dimethylamino-2,2-diphenyl-3,3-dimethyl-1-butyl)urea. (Lu 22-101). MP: 156°–158° C.

N-(3-dimethylamino-2,2-diphenhyl-1-propyl)urea. (Lu 22-069). MP: 173°–175° C.

N-(4-dimethylamino-2,2-bis(4-chlorophenyl)-3-ethyl-1-butyl)urea (Lu 23-028). MP: 108°–110° C.

N-(4-dimethylamino-2,2-bis(4-hydroxyphenyl)-3-methyl-1-butyl)urea.

EXAMPLE 9

Resolution of N-(4-Dimethylamino-2,2-diphenyl-3-methyl-1-butyl)urea. (Lu 9-110)

A. (+)- and (−)-2,2-diphenyl-3-methyl-4-dimethylamino-butanenitrile:

To a solution of 60 g of 2,2-diphenyl-3-methyl-4-dimethylamino-butanenitrile in 400 ml acetone is added 24.3 g L(+)-tartaric acid, and the resulting mixture is stirred until a clear solution is obtained. The mixture is cooled in a refrigerator for 16 hrs., and the resulting crystals are filtered and washed with acetone, to give 46 g of the L(+)-tartrate, melting at 101°–105° C. After two recrystallisations from 400 ml ethanol there is obtained 45 g of L(+)-tartrate, melting at 111°–115° C. The L(+)-tartrate is transformed to the base, which is crystallized from pentane to give 24 g of (−)-2,2-diphenyl-3-methyl-4-dimethylamino-butanenitrile, melting at 102°–103° C. $[\alpha]_D^{22} = -73.3°$, (C=1, MeOH).

The filtrate from the L(+) -tartrate is evaporated and transformed to the base to give 33 g of base. The base is dissolved in 400 ml acetone whereupon 17.8 g of D(−)-tartaric acid is added. The resulting solution is kept overnight in a refrigerator to give 46 g of the D(−)-tartrate, melting at 107°–110° C. After two recrystallizations from 400 ml ethanol there is obtained 43 g of the D(−)-tartrate, melting at 111°–115° C. The D(−)-tartrate is transformed to the base, which is crystallized from pentane to give 24 g of (+)-2,2-diphenyl-3-methyl-4-dimethylamino-butanenitrile, melting at 102°–103° C. $[\alpha]_D^{22} = +72.2°$, (C=1, MeOH).

B. (+)- and (−) -N$^4$,N$^4$-dimethyl-2,2-diphenyl-3-methyl-1,4-butanediamine:

The two enantiomeric nitriles obtained in Example 9A are reduced as described in Example 6 for the corresponding racemate. From 24 g of each nitrile there is obtained from the (+)-nitrile 31 g of (+)-N$^4$,N$^4$-dimethyl-2,2-diphenyl-3-methyl-1,4-butanediamine, dioxalate melting at 185°–186° C. $[\alpha]_D^{22} = +3.4°$, (C=1, DMF). The specific rotation of the corresponding base is $[\alpha]_D^{22} = +10.1°$, (C=2, DMF).

From the (−) -nitrile there is obtained 32 g of (−)-N$^4$,N$^4$-dimethyl-2,2-diphenyl-3-methyl-1,4-butanediamine, dioxalate melting at 185°–186° C. $[\alpha]_D^{22} = -3.0°$, (C=1, DMF). The specific rotation of the corresponding base is $[\alpha]_D^{22} = -9.7°$, (C=2, DMF).

C. (+)- and (−)-N-(4-dimethylamino-2,2-diphenyl-3-methyl-1-butyl)urea. (Lu 23-112 and Lu 23-113):

The two enantiomeric diamines obtained in Example 9B are reacted with potassium cyanate as described for the corresponding racemate in Example 8. After the reaction mixtures have been made basic with 9N sodiumhydroxide, the products are extracted with methylene chloride and dried over magnesium sulfate. After filtration and evaporation in vacuo the products are dissolved in 50 ml ethyl acetate, whereupon there is added 100 ml diisopropylether. The solutions are left overnight in a refrigerator, and the resulting crystals are filtered, washed with diisopropylether and dried.

From 17 g of the (+)-diamine there is obtained 8.5 g of (+)-N-(4-dimethylamino-2,2-diphenyl-3-methyl-1-butyl)urea, melting at 90°–92° C., $[\alpha]_D^{22} = +11.6°$, (C=1, MeOH).

From 25 g of the (−)-diamine there is obtained 13 g of (−)-N-(4-dimethylamino-2,2-diphenyl-3-methyl-1-butyl)urea, melting at 90°–92° C., $[\alpha]_D^{22} = -11.6°$, (C=1, MeOH).

The compound N-(4-dimethylamino-2,2-diphenyl-3-methyl-1-butyl)-urea, (in the following called Lu 9-110), has been tested in mice given several daily/weekly injections against the following experimental model tumors:

P 388 lymphocytic leukaemia
L 1210 lymphoid leukaemia
Ehrlich Ascites tumor (EAT)

| Tumor model | Administration (aqueous solution) | Dose (mg/kg) | ILS % |
|---|---|---|---|
| P 388 | ×1 | 100 | 9 |
| | q 8 hrs × 3 | 100 | 33 |
| | q 3 hrs × 8 | 50 | 67 |
| | i.p. suspension in methylcellulose | | |
| P 388 | q 8 hrs × 6 | 150 | 92 |
| EAT | q 8 hrs × 6 | 150 | 120 |
| L 1210 | q 8 hrs × 6 | 150 | 33 |

| | Toxicity of Lu 9-110 | |
|---|---|---|
| mg/kg | LD$_{10}$ mg/kg | LD$_{50}$ |
| i.p. solution single dose | ~100 | ~150 |
| i.p. solution accumulated dose | 300–500 | 400–600 |
| i.p. suspension accumulated dose (independent of | ~1100 | ~1400 |

-continued schedule)

Preliminary toxicity experiments over 1 and 4 weeks in mice seem to indicate that repeated administration of Lu 9-110 results in only very slight myelosuppression.

The compounds of Formula I and the pharmaceutically acceptable acid addition salts thereof may be administered to animals such as dogs, cats, horses, sheep or the like, including human beings, both orally and parenterally, and may be used for example in the form of tablets, capsules, powders, syrups, or in the form of the usual sterile solutions for injection.

Most conveniently the compounds of Formula I are administered orally in unit dosage form such as tablets or capsules, each dosage unit containing a compound of Formula I or a pharmaceutically acceptable salt thereof in an amount of from about 1 to about 100 mg, most preferably, however, from about 10 to 50 calculated as the free amine.

The compounds of Formula I are usually administered in intervals of from four to ten weeks. The exact individual dosages in a particular case will, of course, be determined according to established medical principles under the direction of a physician. The dosage range for such cytostatic drugs are usually given as weight per squaremeter of body area and normally falls within from about 10 to about 200 milligrams per squaremeter of body area.

When preparing tablets, the active ingredient is for the most part mixed with ordinary tablet adjuvants such as corn starch, potato starch, talcum, magnesium stearate, gelatine, lactose, gums, or the like.

As previously stated, when isolating the compounds of Formula I in the form of an acid addition salt, the acid is preferably selected so as to contain an anion which is non-toxic and pharmacologically acceptable, at least in usual therapeutic doses. Representative salts which are included in this preferred group are the hydrochlorides, hydrobromides, sulphates, acetates, phosphates, nitrates, methanesulphonates, ethane-sulphonates, lactates, citrates, tartrates or bitartrates, embonates and maleates of the amines of Formula I.

Other acids are likewise suitable and may be employed if desired; for example: Fumaric, benzoic, ascorbic, succinic, salicylic, bismethylenesalicylic, propionic, gluconic, malic, malonic, mandelic, cinnamic, citraconic, stearic, palmitic, itaconic, glycolic, benzenesulphonic, and sulphamic acids may also be employed as acid addition saltforming acids.

When it is desired to isolate a compound of the invention in the form of the free base, this may be done according to conventional procedure as by dissolving the isolated or unisolated salt in water, treating with a suitable alkaline material, extracting the liberated free base with a suitable organic solvent drying the extract and evaporating to dryness or fractionally distilling to effect isolation of the free basic amine.

The invention also comprises a method for the alleviation, palliation, mitigation or inhibition of the manifestations of certain physiological-psychological abnormalies of animals by administering to a living animal body, including human beings, an adequate quantity of a compound of Formula I or a non-toxic acid addition salt thereof. An adequate quantity would be from about 5 mg to about 100 mg per squaremeter of body area in each unit dosage, and from about 15 milligrams to about 300 milligrams/squaremeter of body area every fourth to sixth week.

It is to be understood that the invention is not limited to the exact details of operation or exact compound or compositions shown and described, as obvious modifications and equivalents will be apparent to one skilled in the art.

We claim:

1. A compound selected from the group consisting of:
(a) a urea derivative of the following formula:

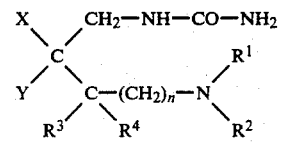

wherein X and Y are the same or different and are selected from the group consisting of a phenyl group, each of said phenyl groups being optionally substituted with one or two groups selected from halogen, $CF_3$, OH, or alkoxy(1-4 C-atoms); and $R^1$ and $R^2$ are the same or different, and are each selected from the group consisting of lower alkyl groups having from one to four carbon atoms inclusive, or they form together with the nitrogen atom a saturated five- or six-membered heterocyclic ring; $R^3$ and $R^4$ are each selected from hydrogen, lower alkyl or alkenyl groups with from 1-6 carbon atoms inclusive, cyclopentyl or cyclohexyl; and n is 0 or 1, and
(b) a pharmaceutically acceptable acid addition salt thereof.

2. A compound according to claim 1, wherein X and Y are phenyl groups optionally substituted with chlorine or fluorine in the para-positions, $R^1$ and $R^2$ are methyl groups, $R^3$ is a methyl or ethyl group, $R^4$ is hydrogen and "n" is 0 or 1.

3. A compound of claim 1 which is N-(4-dimethylamino-2,2-diphenyl-3-methyl-1-butyl)urea, acid addition salts thereof and enantiomers.

4. A compound of claim 1 which is N-(4-diisopropylamino-2,2-diphenyl-3-methyl-1-butyl)urea, acid addition salts thereof and enantiomers.

5. A compound of claim 1 which is N-(4-dimethylamino-2,2-diphenyl-3-ethyl-1-butyl)urea, acid addition salts thereof and enantiomers.

6. A compound of claim 1 which is N-(4-dimethylamino-2,2-bis(4-chlorophenyl)-3-ethyl-1-butyl)urea, acid addition salts thereof and enantiomers.

7. A compound of claim 1 which is N-(4-dimethylamino-2,2-bis(4-hydroxyphenyl)-3-methyl-1-butyl)urea, acid addition salts thereof and enantiomers.

8. A pharmaceutical composition in unit dosage form comprising as an active ingredient a compound as defined in claim 1 in an amount of from 0.10 to 100 mg per unit dosage, and one or more pharmaceutical diluents or carriers.

9. A pharmaceutical composition according to claim 8, comprising as an active ingredient a compound as defined in claim 3.

* * * * *

UNITED STATES PATENT AND TRADEMARK OFFICE
CERTIFICATE OF CORRECTION

PATENT NO. : 4,650,900

DATED : March 17, 1987

INVENTOR(S) : Niels Lassen, Klaus P. Bogeso and Klaus G. Jensen

It is certified that error appears in the above-identified patent and that said Letters Patent is hereby corrected as shown below:

Col. 8, line 61 (first column); delete "mg/kg" (first occurrence)

Col. 8, line 61 (third column); "$LD_{50}$" should read -- $LD_{50}$ mg/kg --

Signed and Sealed this

Twenty-second Day of March, 1988

Attest:

DONALD J. QUIGG

*Attesting Officer*   *Commissioner of Patents and Trademarks*